(12) United States Patent
Mizokuchi

(10) Patent No.: US 10,508,991 B2
(45) Date of Patent: Dec. 17, 2019

(54) POLARIZATION ANALYSIS APPARATUS AND CONTROL METHOD OF POLARIZATION ANALYSIS APPARATUS

(71) Applicant: Tianma Japan, Ltd., Kanagawa (JP)

(72) Inventor: Chikaaki Mizokuchi, Kanagawa (JP)

(73) Assignee: TIANMA JAPAN, LTD., Kanagawa (JP)

( * ) Notice: Subject to any disclaimer, the term of this patent is extended or adjusted under 35 U.S.C. 154(b) by 0 days.

(21) Appl. No.: 16/371,403

(22) Filed: Apr. 1, 2019

(65) Prior Publication Data

US 2019/0302023 A1 Oct. 3, 2019

(30) Foreign Application Priority Data

Mar. 30, 2018 (JP) .................................. 2018-066892

(51) Int. Cl.
  *G01J 4/00* (2006.01)
  *G01N 21/64* (2006.01)
  *G02F 1/13* (2006.01)
  *G01J 3/02* (2006.01)

(52) U.S. Cl.
  CPC ........ *G01N 21/6445* (2013.01); *G01J 3/0224* (2013.01); *G01J 4/00* (2013.01); *G02F 1/13* (2013.01)

(58) Field of Classification Search
  CPC ...... G01N 21/6445; G01J 3/0224; G01J 4/00; G02F 1/13

USPC .......................................................... 356/364
See application file for complete search history.

(56) References Cited

U.S. PATENT DOCUMENTS

| 9,719,927 B2 * | 8/2017 | Hibara | ...................... G02F 1/13 |
| 2005/0200941 A1 * | 9/2005 | Yao | ........................... G01J 4/00 |
| | | | 359/301 |
| 2017/0074796 A1 * | 3/2017 | Hibara | ...................... G02F 1/13 |

FOREIGN PATENT DOCUMENTS

WO  WO 2015/174332  11/2015

* cited by examiner

*Primary Examiner* — Roy M Punnoose
(74) *Attorney, Agent, or Firm* — Young & Thompson

(57) ABSTRACT

A polarization analysis apparatus includes: a light source that radiates light to a sample; a liquid crystal panel that outputs polarized light in a specific direction from light radiated from an excited state sample; an image sensor that measures a luminance of polarized light; and a controller that controls the liquid crystal panel and the image sensor. The controller calculates a reference voltage of a rectangular wave; calculates a corrected reference voltage by correcting the reference voltage in the rectangular wave where an absolute value of the reference voltage changes in response to a phase change; applies the reference voltage and the corrected reference voltage to the liquid crystal panel; operates the image sensor in accordance with a light exposure time to measure luminance of polarized light; and calculates a degree of polarization of the sample based on results of the measurement.

16 Claims, 5 Drawing Sheets

POLARIZATION ANALYSIS APPARATUS AND CONTROL METHOD OF POLARIZATION ANALYSIS APPARATUS

CROSS-REFERENCE TO RELATED APPLICATIONS

This Non-provisional application claims priority under 35 U.S.C. § 119(a) on Patent Application No. 2018-66892 filed in Japan on Mar. 30, 2018, the entire content of which is hereby incorporated by reference.

BACKGROUND

The present invention relates to a polarization analysis apparatus that can be used for the fluorescence polarization immunoassay.

A polarization analysis apparatus used for the fluorescence polarization immunoassay and the like is configured to radiate light to a sample from a light source such as a laser. The polarization analysis apparatus measures a polarization component $I_∥$ parallel to the polarization direction of incident light (excitation light) radiated from the sample and a polarization component $I_⊥$ perpendicular to the polarization direction of incident light (excitation light), and calculates the degree of polarization based on the two polarization components. The apparatus can also estimate the degree of liquid viscosity and the like based on the degree of polarization.

SUMMARY OF THE INVENTION

WO 2015/174332 discloses a polarization analysis apparatus that can simultaneously measure multiple points. The polarization analysis apparatus of WO2015/174332 has a polarization selection element that selects polarized light of a specific direction from the measurement light radiated by the sample by applying a voltage based on a drive signal. The polarization analysis apparatus of WO2015/174332 also has an image sensor that receives the polarized light selected by the polarization selection element.

If the drive signal is a sine wave signal with a cycle T1, as illustrated in FIG. 10, the polarized light with the luminance changing in a sine waveform enters the image sensor. The horizontal axis of the graph illustrated in FIG. 10 indicates the time, and the vertical axis illustrates the magnitude of the luminance of the measurement light that passes through the polarization selection element. The image sensor outputs the luminance data $I_1$, $I_2$, $I_3$, and $I_4$ as illustrated in FIG. 11. The horizontal axis of the graph illustrated in FIG. 11 indicates the time, and the vertical axis illustrates the integral value of the luminance measured during the light exposure time.

Here, the X axis and the Y axis are given to the plane of the polarization selection element. The luminance of the polarized light in the direction parallel to the X axis is $I_∥$, and the luminance of the polarized light in the direction parallel to the Y axis is $I_⊥$. WO2015/174332 describes that the degree of polarization P can be calculated by Formula 1 if the phase relationship between the image sensor and the polarization selection element can be controlled with a high degree of accuracy and the polarized light satisfies prescribed conditions.

Formula 1

$$P = \frac{(I_∥ - I_⊥)}{(I_∥ + I_⊥)} = \frac{(I_3 - I_1)}{(I_3 + I_1)} \quad (1)$$

WO2015/174332 also describes that even if the phase relationship cannot be controlled, if a sine wave signal is input as the drive signal, the degree of polarization P can be calculated by Formula 2 regardless of the phase relationship. Here, the values AC and DC can be calculated by Formula 3 and Formula 4, respectively.

Formula 2

$$P = \frac{AC}{DC \times 2} \quad (2)$$

Formula 3

$$AC = \sqrt{\{(I_1 - I_3)^2 - (I_2 - I_4)^2\}} \quad (3)$$

Formula 4

$$DC = \frac{I_1 + I_2 + I_3 + I_4}{4} \quad (4)$$

An aspect of this disclosure is an optical element comprising: A polarization analysis apparatus comprises: a light source that radiates first light causing a sample to be in an excitation state; a polarization selection element that outputs polarized light in a specific direction from second light radiated from the excited state sample in response to a voltage applied based on control information on a rectangular wave, the rectangular wave oscillates between positive and negative and an absolute value changes in a first cycle; an image sensor that measures a luminance of polarized light that has passed through the polarization selection element; and a controller that controls the polarization selection element and the image sensor. The controller is configured to: calculate a reference voltage for each phase of the rectangular wave to cause the polarization selection element to output polarized light such that a change in luminance thereof forms a sine wave that oscillates in the first cycle; calculate a corrected reference voltage by correcting the reference voltage in at least one of two sections of the rectangular wave where an absolute value of the reference voltage increases in response to a phase change and where an absolute value of the reference voltage decreases in response to the phase change; generate the control information on the rectangular wave based on the reference voltage and the corrected reference voltage; apply a voltage to the polarization selection element based on the control information on the rectangular wave; operate the image sensor in accordance with a light exposure time having a time width obtained by dividing the first cycle by four, and measure luminance of polarized light output from the polarization selection element; and calculate a degree of polarization of the sample based on results of the measurement.

It is to be understood that both the foregoing general description and the following detailed description are exemplary and explanatory and are not restrictive of this disclosure.

DETAILED DESCRIPTION OF THE EMBODIMENTS

Figure 1:
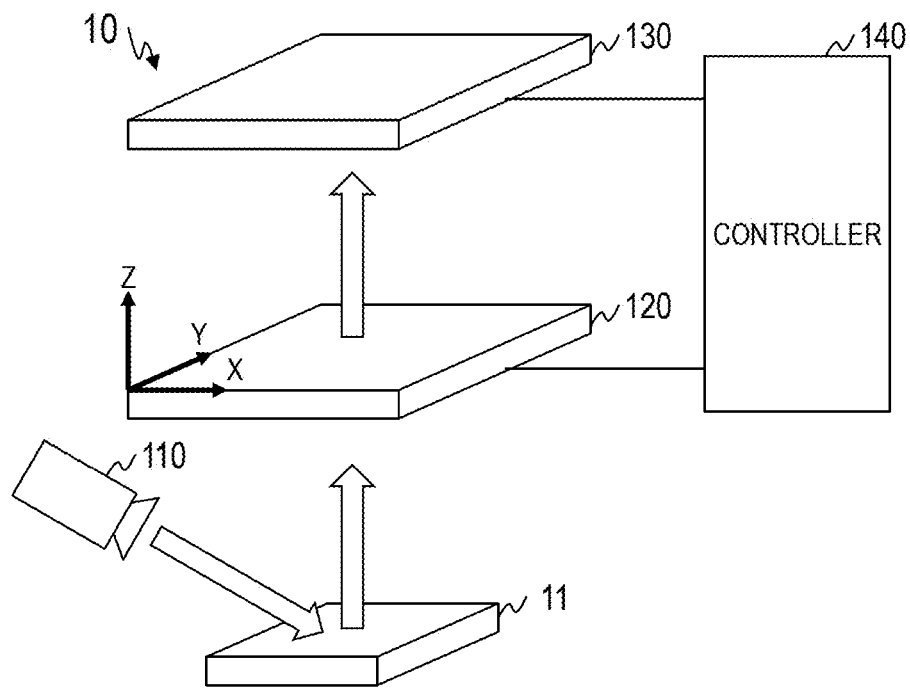
FIG. 1 illustrates a configuration example of a polarization analysis apparatus of the present invention.

Below, embodiments of the present invention will be explained with reference to figures. However, the present invention shall not be interpreted as limited to the descriptions of embodiments below. It is easily understood by a person skilled in the art that the specific configurations of the present invention can be modified without departing from the concept and scope of the present invention.

In the descriptions of the present invention below, the same or similar configurations and functions are given the same reference characters, and the overlapping descriptions will not be repeated.

Embodiment 1

In Embodiment 1, a representative of the rectangular signal correction method of the present invention will be explained.

Figure 2:
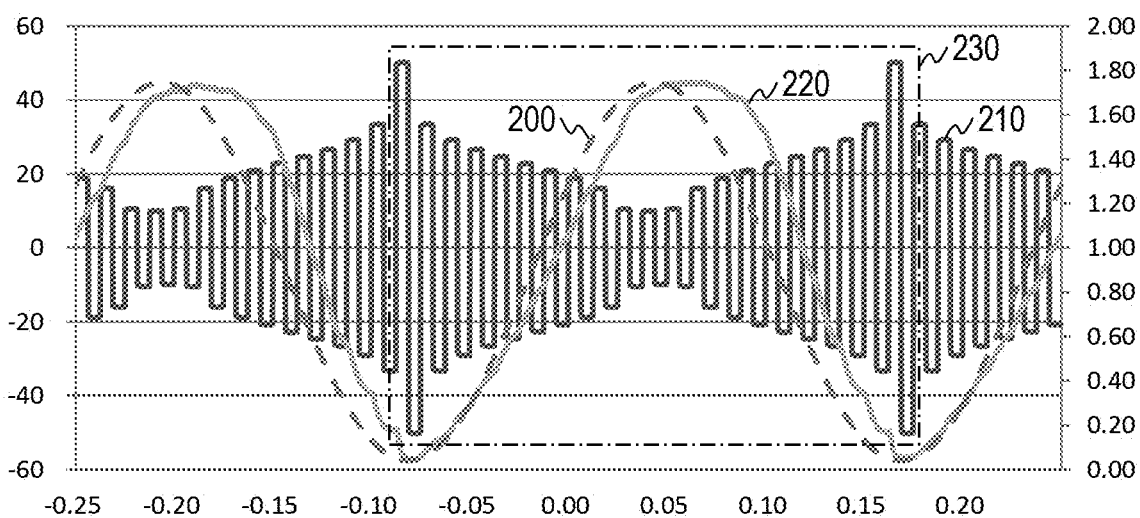
FIG. 2 is a graph illustrating the output of polarized light in a case of applying a drive signal before correction to the polarization selection element of the present invention.

FIG. 1 illustrates a configuration example of a polarization analysis apparatus of the present invention. FIG. 2 is a graph indicating the output of polarized light in a case of applying a voltage of a rectangular wave before correction to a polarization selection element of the present invention. The left vertical axis of the graph of FIG. 2 indicates the voltage, the right vertical axis indicates the luminance, and the horizontal axis indicates the time.

A polarization analysis apparatus 10 of the present invention includes a light source 110, a polarization selection element 120, an image sensor 130, and a controller 140. An optical system such as an object lens may also be disposed between a sample 11 and the polarization selection element 120.

The light source 110 radiates light to excite the sample 11 to be measured. The light source 110 is a laser or the like, for example. Light radiated from the light source 110 is selected in accordance with the type and state of the sample 11.

The sample 11 includes a fluorescent substance, excites by the light radiated from the light source 110, and radiates light. The polarization direction of the measurement light that was output by the sample 11 changes depending on the temperature and viscosity of the sample 11 as well as the amounts and types of substances contained in the sample 11. In the present invention, the measurement light in which $I_{\parallel}$ is larger than $I_{\perp}$ is constantly radiated from the sample 11.

The polarization selection element 120 is driven by a voltage applied based on the drive signal, and outputs measurement light of a specific polarization direction out of the measurement light radiated from the sample 11. The polarization selection element 120 is disposed between the sample 11 and the image sensor 130. The polarization selection element 120 is made of a liquid crystal panel of a transmissive type and a polarization panel. In the present invention, the liquid crystal panel is a TN-type liquid crystal panel.

As illustrated in FIG. 1, in the present invention, the X axis and Y axis are set in the plane of the polarization selection element 120, and the Z axis is set in the direction perpendicular to the XY plane and parallel to the travelling direction of the measurement light.

Figure 11:
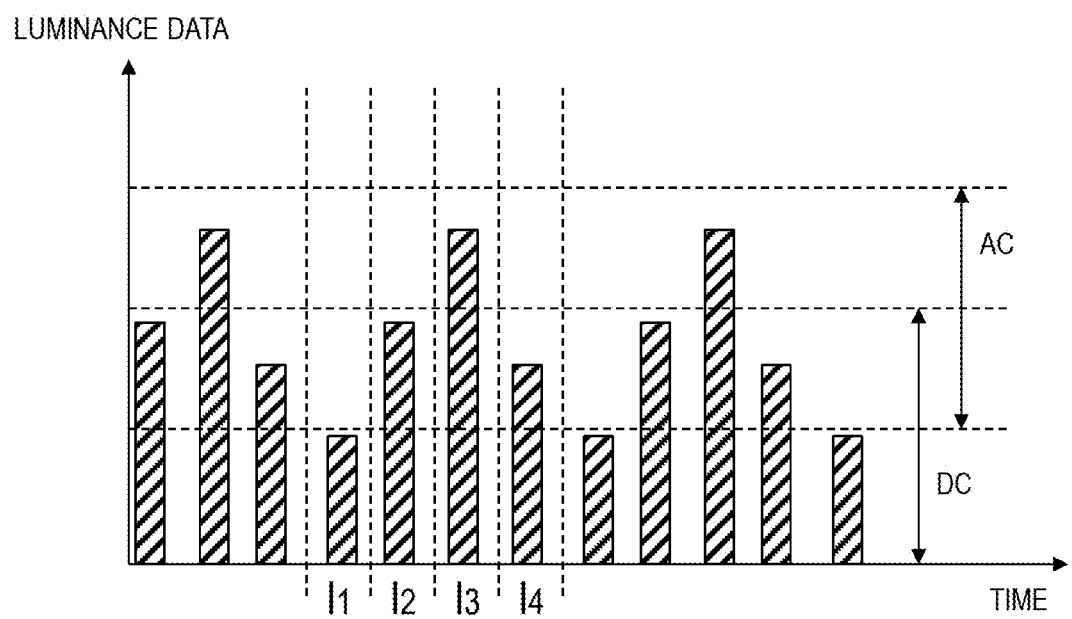
FIG. 11 is a graph illustrating data of the polarized light of the prior art.

The image sensor 130 is a sensor including a plurality of light-receiving elements such as CCD sensor, CMOS sensor, and photo-diode array. The image sensor 130 measures the luminance of the measurement light output from the polarization selection element 120 based on the predetermined light exposure time, and outputs the measurement results as the luminance data. The image sensor outputs the luminance data as illustrated in FIG. 11.

The controller 140 applies a voltage to the polarization selection element 120 based on the drive signal and controls the light exposure time of the image sensor 130. The controller 140 includes, for example, a computer having a processor and a memory, a power supply that supplies a voltage to the polarization selection element 120 based on the drive signal, and a function generator that controls the light exposure time of the image sensor 130. The controller 140 controls the drive signal and the light exposure time such that the phase relationship between the two remains constant.

The relationship between the drive signal and the light exposure time will be explained below.

Figure 10:
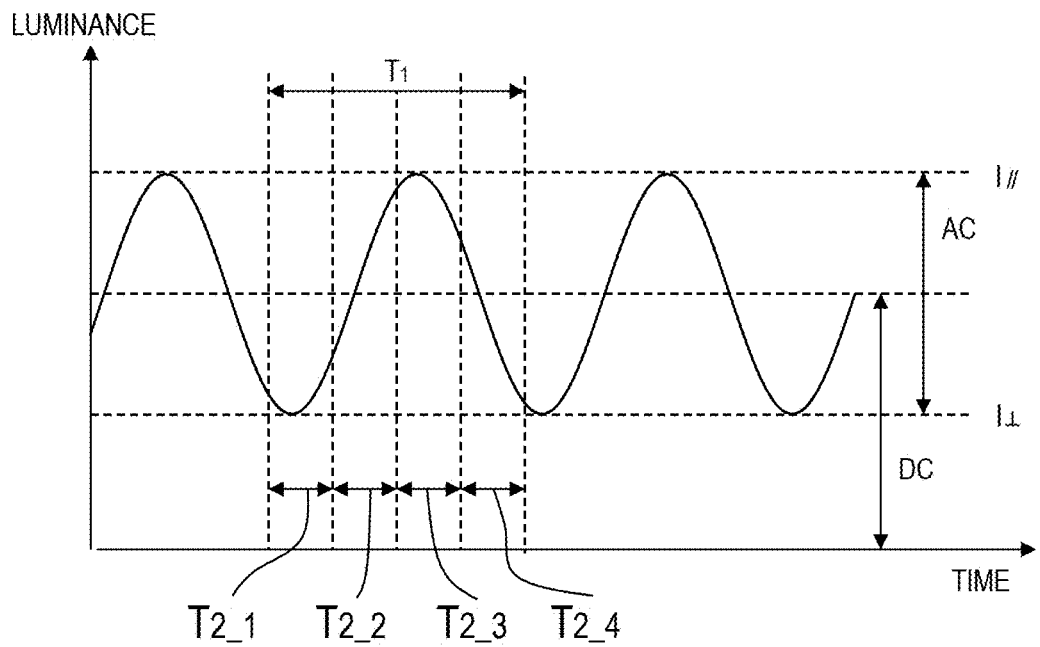
FIG. 10 is a graph illustrating the change in luminance of the polarized light of the prior art.

The controller 140 generates control information of the drive signal for obtaining the output of the measurement light with the luminance changing in a sine waveform as illustrated in FIG. 10, and supplies a voltage to the polarization selection element 120 based on the control information of the drive signal. The drive signal oscillates in a cycle of T1. The cycle of the drive signal synchronizes with the cycle of the output (luminance change) of measurement light. The controller 140 divides the cycle T1 into four sections, and sets each time section $T_{2-1}$, $T_{2-2}$, $T_{2-3}$, and $T_{2-4}$ as the light exposure time of the image sensor 130. The controller 140 obtains the luminance data from the image sensor 130, and calculates the degree of polarization by plugging the luminance into Formula 1 or Formula 2.

If there is a constant relationship between the phase of the luminance change of the measurement light that passes through the polarization selection element 120 and the light-receiving timing (phase) of the measurement light, the degree of polarization P can be calculated using Formula 1. If there is no constant relationship between the phase of the measurement light that passes through the polarization selection element 120 and the light-receiving timing (phase) of the measurement light, the degree of polarization P can be calculated using Formula 2.

The relationship between the drive signal and the measurement light that passes through the polarization selection element 120 will be explained below.

Here, a rectangular wave 210 as illustrated in FIG. 2 is used for the drive signal such that the measurement light with the luminance changing in a sine waveform is output, which is indicated by the signal 200. In the rectangular wave 210, the voltage oscillates between positive and negative, and the absolute value of the voltage changes at cycles. The absolute value of the voltage changes at a cycle of T1. In the present invention, the rectangular wave is also referred to as a rectangular signal.

In the present invention, the rectangular signal 210 within the range 230 is considered a rectangular signal 210 of one cycle. The left end of the range 230 is 0, and the right end thereof is 2n. The cycle in which the rectangular signal 210 oscillates between positive and negative (pulse width) is smaller than the cycle T1.

A signal 220 indicates the shape of the luminance change of the measurement light that passes through the liquid crystal panel, which is affected by the delayed response of the liquid crystal panel to the voltage change. As illustrated in FIG. 2, the signal 220 is offset from the signal 200. The offset amount is greater in sections of the rectangular signal 210 where the absolute value of the voltage is increasing in response to the change in phase. In the present invention, the section of the rectangular signal 210 where the absolute value of the voltage is increasing in response to the change in phase is referred to as an ascending section of the rectangular signal 210, and the section of the rectangular signal 210 where the absolute value of the voltage is decreasing in response to the change in phase referred to as a descending section of the rectangular signal 210.

The offset described above deteriorates the calculation accuracy of the degree of polarization P. That is because the prerequisite of Formula 2 is not satisfied. In the present invention, the phase in the ascending section of the rectangular signal 210 is from n to 2n.

In order to solve this problem, the controller 140 of the present invention corrects the rectangular signal 210 to eliminate the offset, and applies a voltage to the polarization selection element 120 based on the corrected rectangular signal.

Next, the process performed by the controller 140 to calculate the corrected rectangular signal will be explained.

(Process 1) The controller 140 fits a relationship (VT characteristic) between the applied voltage and transmittance of the liquid crystal panel used for the polarization selection element 120 to the sigmoid curve, and then calculates an inverse function representing the voltage with the luminance as a variable. In the present invention, the voltage is x, the luminance is y, the function representing the luminance y is F(x) and the inverse function thereof is G(y).

The controller 140 of the present invention performs the fitting using the Boltzman function of Formula 5, and calculates the inverse function as Formula 6. Here, A1, A2, and x0 are adjustable parameters.

Formula 5

$$y = A2 + \frac{(A1 - A2)}{\left(1 + \exp\left(\frac{(x - x0)}{dx}\right)\right)} \quad (5)$$

Formula 6

$$x = dx \cdot \ln\left(\frac{A1 - A2}{y - A2} - 1\right) + x0 \quad (6)$$

(Process 2) The controller 140 plugs the luminance y at the phase p in the measurement light output model H(p) illustrated in FIG. 10 into the inverse function G(y), thereby calculating the voltage x. In the present invention, the measurement light output model H(p) is given by Formula 7. The controller 140 calculates the voltage at the phase p of the rectangular signal 210 to realize the luminance H(p) by plugging the luminance H(p) into the variable y in Formula 6. In the present invention, the voltage corresponding to the amplitudes of the rectangular signal 210 will also be referred to as the reference voltage. The controller 140 performs the same process for each phase. The controller 140 holds the information including the calculated reference voltage and the oscillation cycle of the rectangular signal as the control information of the drive signal. The oscillation cycle of the rectangular signal is determined in advance.

Formula 7

$$H(p) = \frac{\sin((p - 0.5)\pi)}{2} \quad (7)$$

(Process 3) The controller 140 calculates the first corrected reference voltage obtained by correcting the reference voltage in the ascending section of the rectangular signal 210. In Embodiment 1, the value obtained by adding a predetermined fixed value to the reference voltage is calculated as the first corrected reference voltage. Examples of the fixed value include "+0.4V."

(Process 4) The controller 140 updates the control information of the drive signal based on the calculation results of the first corrected reference voltage.

Figure 3:
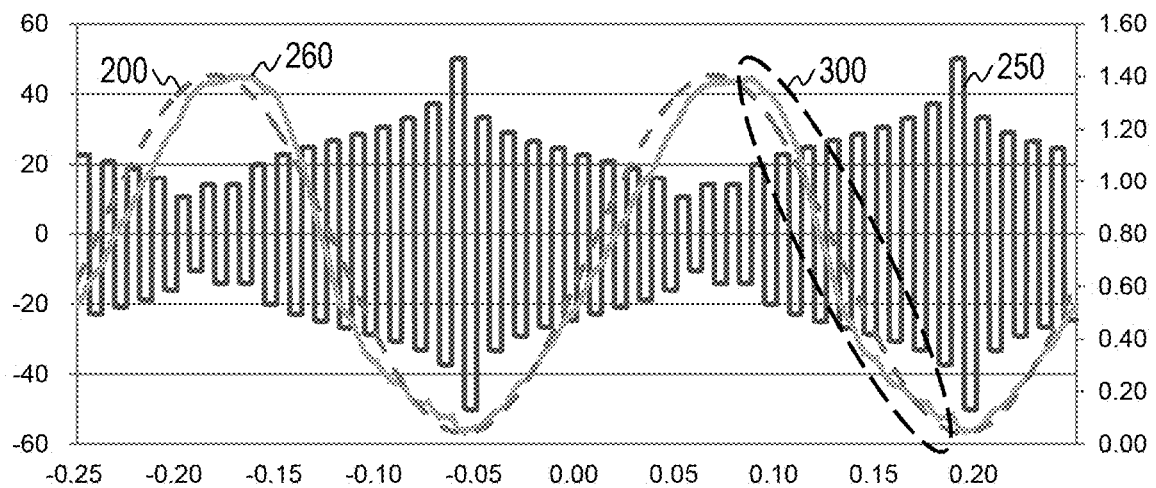
FIG. 3 is a graph illustrating the change in luminance of the polarized light in a case of applying a drive signal after correction to the polarization selection element of the present invention.

The controller 140 applies a voltage to the polarization selection element 120 based on the control information of the drive signal generated by the processes described above. FIG. 3 is a graph illustrating the change in luminance of the polarized light in a case of applying a voltage of a rectangular wave after correction to the polarization selection element of the present invention.

When a voltage based on a rectangular signal 250, which is obtained by correcting the reference voltage in the ascending section of the rectangular signal 210, is applied to the polarization selection element 120, the change in luminance of measurement light that passes through the polarization selection element 120 is represented by a graph such as the signal 260. As illustrated in FIG. 3, the offset between the signal 200 and the signal 260 is smaller than the offset between the signal 200 and the signal 220.

As described above, according to Embodiment 1, the controller 140 controls the voltage to be applied to the polarization selection element 120 based on the rectangular signal obtained by correcting the reference voltage in the ascending section of the rectangular signal 210, and therefore, the change in luminance of the measurement light that passes through the polarization selection element 120 forms an ideal sine wave. As a result, the calculation accuracy of the degree of polarization is improved.

Embodiment 2

In Embodiment 1, the rectangular signal 210 is corrected only in the ascending sections. In Embodiment 2, the rectangular signal 210 is also corrected in the descending sections. Below, Embodiment 2 will be explained mainly focusing on the differences from Embodiment 1.

The configuration of the polarization analysis apparatus 10 of Embodiment 2 is the same as that of Embodiment 1, and the description will therefore be omitted.

In Embodiment 2, the controller 140 calculates the second corrected reference voltage obtained by correcting the reference voltage in the descending section of the rectangular signal 210 together with the first corrected reference voltage in (Process 3). In Embodiment 2, the value obtained by adding a predetermined fixed value to the reference voltage is calculated as the second corrected reference voltage. Examples of the fixed value include "−0.2V."

According to Embodiment 2, the voltage is corrected in different manners in the ascending sections and the descending sections of the rectangular signal 210, and as a result, the change in luminance of the measurement light that passes through the polarization selection element 120 is made closer to an ideal sine wave.

Embodiment 3

In Embodiment 1, the controller 140 is configured to uniformly correct the reference voltage in the ascending sections of the rectangular signal 210. However, when the reference voltage is corrected uniformly, the overshoot occurs as indicated with the region 300 of FIG. 3. In Embodiment 3, the controller 140 is configured to correct the reference voltage in the ascending sections of the rectangular signal 210 so as to suppress the occurrence of the overshoot. Below, Embodiment 3 will be explained mainly focusing on the differences from Embodiment 1.

The configuration of the polarization analysis apparatus 10 of Embodiment 3 is the same as that of Embodiment 1, and the description thereof will therefore be omitted.

In Embodiment 3, the controller 140 calculates the first corrected reference voltage in which the correction amount gradually changes in accordance with the phase change of the rectangular signal 210. Specifically, the controller 140 corrects the reference voltage such that the correction amount is greatest at the start of the ascending section of the rectangular signal 210 and then gradually decreases toward the end of the ascending section. That is, the reference voltage is corrected such that the correction amount decreases as the phase increases (corresponding to the phase change).

Figure 4:
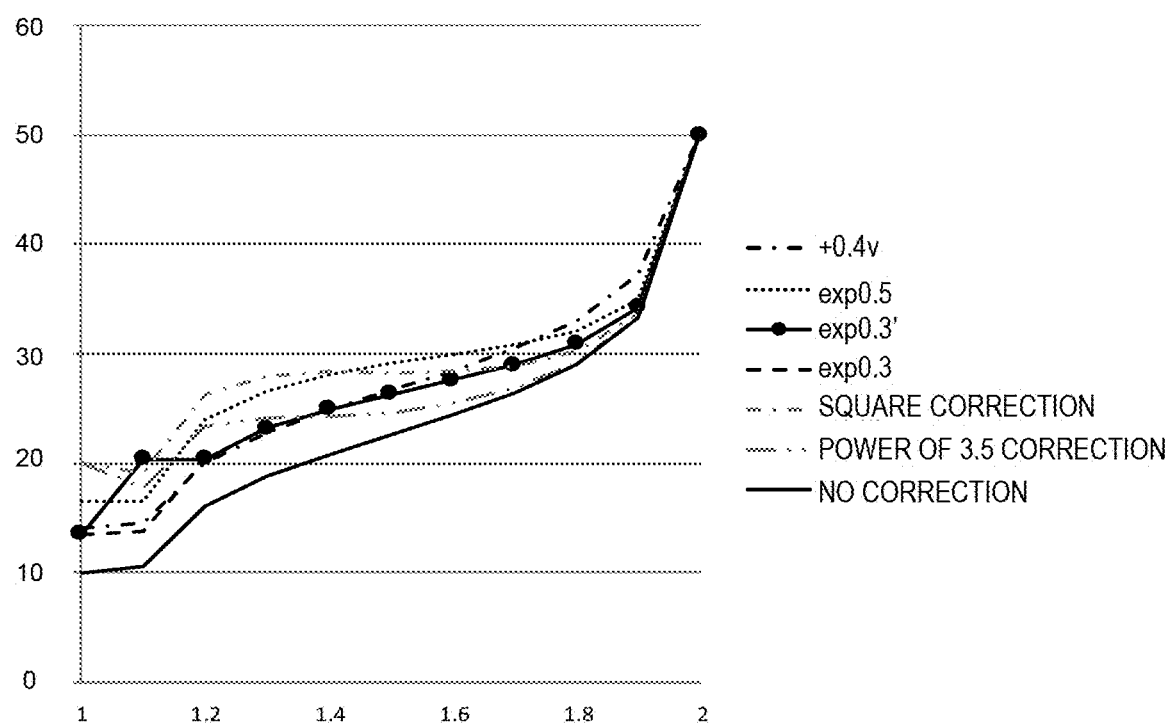
FIG. 4 is a diagram illustrating a relationship between phase and correction amount of a rectangular signal of the present invention.
Figure 5:
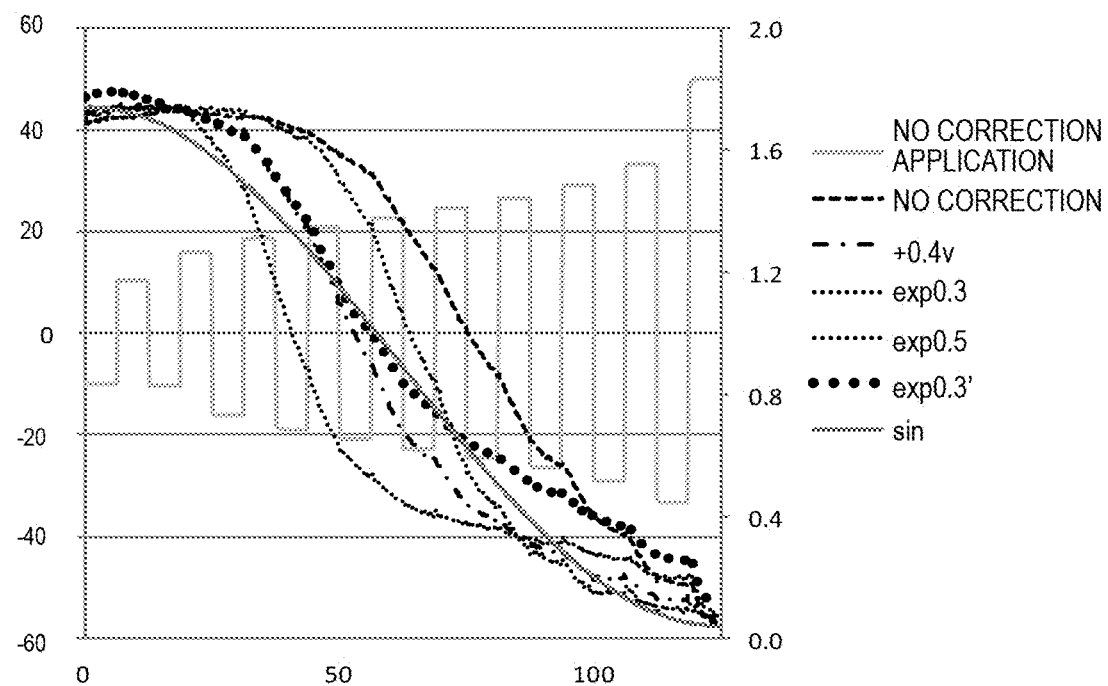
FIG. 5 is a graph illustrating a relationship between correction methods and correction results of the rectangular signal of the present invention.

FIG. 4 is a diagram illustrating a relationship between the phase and the correction amount of the rectangular signal 210 of the present invention. FIG. 5 is a graph illustrating a relationship between the correction methods and the correction results of the rectangular signal of the present invention. In FIG. 4, the vertical axis indicates the voltage, and the horizontal axis indicates the phase. In FIG. 5, the left vertical axis indicates the voltage, the right vertical axis indicates the luminance, and the horizontal axis indicates the time.

In Embodiment 3, five correction methods are employed. "+0.4 v correction" is the correction method of the rectangular signal 210 described in Embodiment 1.

The "expG correction" is the correction method to calculate the first corrected reference voltage based on Formula 8. G is a parameter used for the correction. In the formula, p is the phase, V is the reference voltage of the rectangular signal 210 at the phase p, and V' is the corrected reference voltage at the phase p (first corrected reference voltage). Thus, in the "exp0.5 correction," the reference voltage in the ascending section of the rectangular signal 210 is corrected based on Formula 8 where G is 0.5.

Formula 8

$$V'=V\times\exp((2-p)\times G) \quad (8)$$

The "exp0.3' correction" is the correction method using the same formula as that of "exp0.3," where the correction is made such that the first corrected reference voltage of $0.9\pi$ becomes equivalent to the first corrected reference voltage of $0.8\pi$.

The "power of q correction" is the correction method to calculate the first corrected reference voltage based on Formula 9. q is a parameter used for the correction.

Formula 9

$$V'=V\times(2-p)^q \quad (9)$$

As illustrated in FIG. 5, in the "expG correction," the problem of overshoot is solved when G is 0.3 or smaller. In terms of the "power of q correction," the study on q being greater than 2 and smaller than 10 reveals that the problem of overshoot is more effectively solved when q is 3.5.

According to Embodiment 3, the reference voltage of the ascending sections of the rectangular signal 210 is corrected such that the correction amount for the reference voltage changes gradually depending on the phase change of the rectangular signal 210, which makes it possible to prevent the problem of overshoot. Thus, it is possible to make the waveform of the luminance change of the measurement light that passes through the polarization selection element 120 even closer to the sine wave as compared to the case in which the correction is made uniformly.

Embodiment 4

Embodiment 4 differs from Embodiment 1 in the calculation method of the function used for fitting the corrected reference voltages (first corrected reference voltage and the second corrected reference voltage). Below, Embodiment 4 will be explained mainly focusing on the differences from Embodiment 1.

The configuration of the polarization analysis apparatus 10 of Embodiment 4 is the same as that of Embodiment 1, and the description thereof will therefore be omitted.

In Embodiment 4, the function used in (Process 1) differs from that of Embodiment 1. Specifically, the controller 140 of the present invention performs the fitting using the Hill function as in Formula 10, and calculates the inverse function as in Formula 11. Here, k and n are adjustable parameters.

Formula 10

$$y = \frac{x^n}{k^n + x^n} \quad (10)$$

Formula 11

$$x = k \times \left(\frac{y}{1-y}\right)^{\frac{1}{n}} \quad (11)$$

(Process 2) is the same as that of Embodiment 1. Specifically, the controller 140 calculates the reference voltage at the phase p of the rectangular signal 210 to realize the luminance H(p) by plugging the output model H(p) of the measurement light illustrated in FIG. 10 into the variable y in Formula 11.

Figure 6:
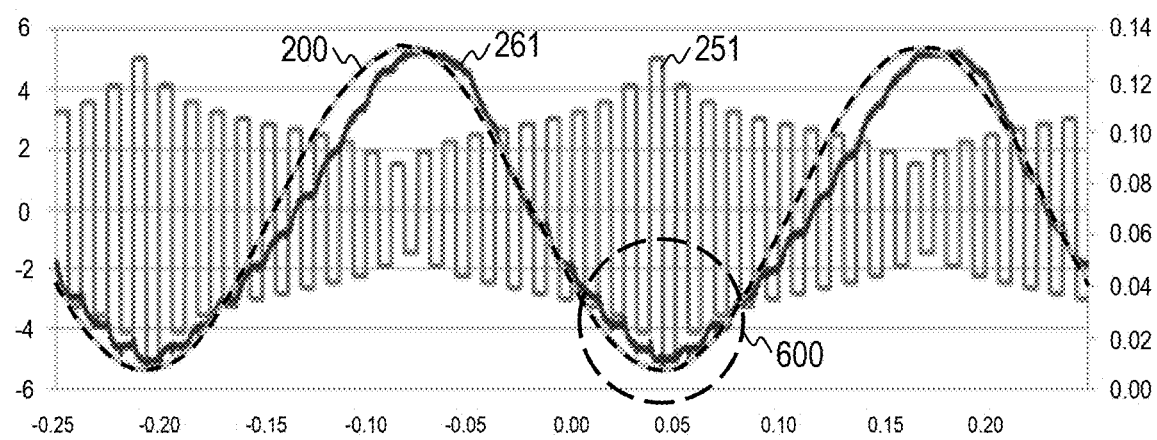
FIG. 6 is a graph illustrating the change in luminance of the polarized light in a case of inputting a drive signal fitted using Hill function to the polarization selection element of the present invention.

When the Hill function is used for fitting, the offset between the signal 200 and the signal 261 in the region 600 of FIG. 6 indicating a region near the point of the greatest absolute value of the voltage is smaller as compared to the case in which the Boltzmann function is used for fitting. On the other hand, a great offset occurs in a region near the point of the smallest absolute value of the voltage of the rectangular signal 251, and the correction value is added to the reference voltage to eliminate this offset.

When the Hill function is used for fitting, the symmetrical offset between the signal 200 and the signal 261 in the region 600 of FIG. 6 indicating a region near the point of the greatest absolute value of the voltage can be solved by adjusting the parameters k and n in Formula 11. On the other hand, a great asymmetrical offset occurs in a region near the point of the smallest absolute value of the voltage of the rectangular signal 251, and the correction value is added to the reference voltage to eliminate this offset.

In (Process 3), the controller 140 calculates the correction value to be added to the reference voltage in the ascending section of the rectangular signal 251, using the fractional function with the phase p as a variable. In Embodiment 4, the correction value to be added to the reference voltage is calculated using the fractional function of Formula 12. In the formula, K, a, b, c, and d are adjustable parameters.

Formula 12

$$\text{CORRECTION VALUE} = K \frac{(cy+d)}{y^2 + ay + b} \quad (12)$$

Figure 7:
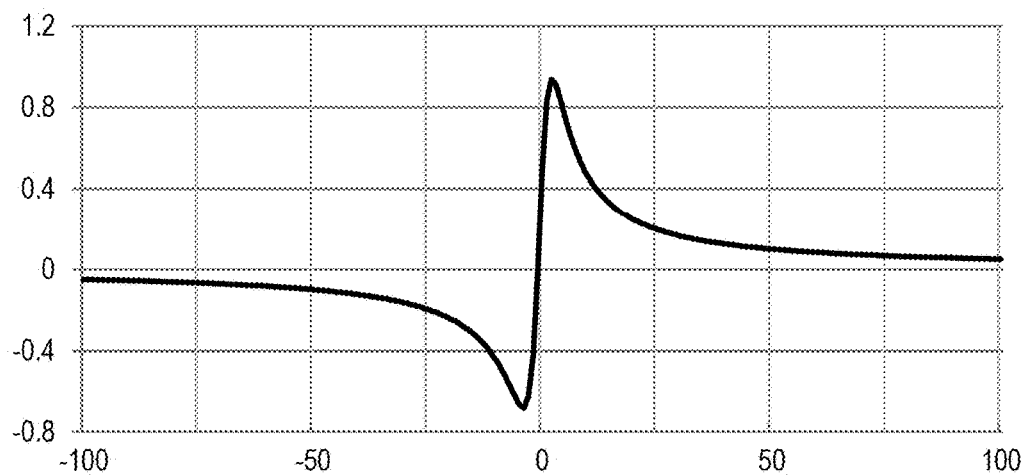
FIG. 7 illustrates an example of the fractional function.

FIG. 7 illustrates an example of the fractional function. The vertical axis indicates the correction value, and the horizontal axis indicates the value of the variable y. As illustrated in FIG. 7, the correction value has characteristics of drastically changing near y=0 and converging to 0 at infinity on the horizontal axis.

The possible parameter values are as follows: a, c, d are each 1, b is 10, and K is 5.

In order to eliminate the offset in the ascending sections of the rectangular signal 251, the correction needs to be made such that the applied voltage rises quickly, and in order to eliminate the offset in the descending sections of the rectangular signal 251, the correction needs to be made such that the applied voltage goes down quickly. Thus, the controller 140 calculates the corrected reference voltage by adding, to the reference voltage, the correction value derived from the fractional function having the characteristics illustrated in FIG. 7.

In the present invention, the variable y in Formula 12 is substituted by the phase p. The variable y may also be substituted by a value obtained by adding an arbitrary phase θ to the phase p. θ is an adjustable parameter.

Figure 8:
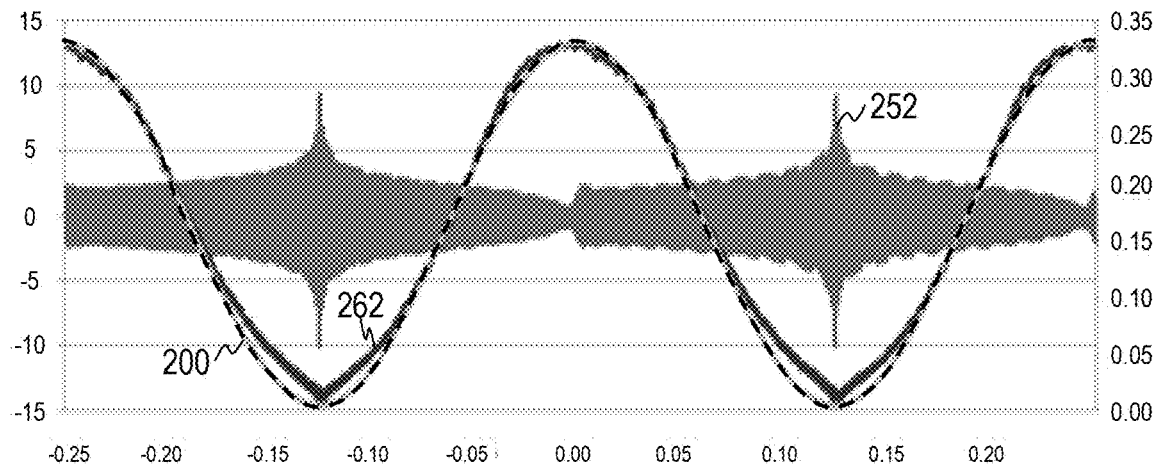
FIG. 8 is a graph illustrating an output of the polarized light in a case of applying a drive signal after correction to the polarization selection element of the present invention.

FIG. 8 is a graph illustrating an output of the polarized light in a case of applying a drive signal after correction to the polarization selection element of the present invention.

As illustrated in FIG. 8, each region near the point of the smallest absolute value of the voltage in the rectangular signal 252 has a shape indicating the characteristic of the fractional function. When a voltage is applied based on the rectangular wave 252 as illustrated in FIG. 8, the offset between the signal 200 and the signal 262 is smaller than the offset between the signal 200 and the signal 261.

According to Embodiment 4, by using the Hill function for fitting and the fractional function for correction, the change in luminance of the measurement light that passes through the polarization selection element 120 can be made even closer to the ideal sine wave efficiently and easily.

Embodiment 5

Embodiment 5 differs from Embodiment 1 in using an FFS (fringe field switching) liquid crystal panel. Below, Embodiment 5 will be explained mainly focusing on the differences from Embodiment 1.

Figure 9:
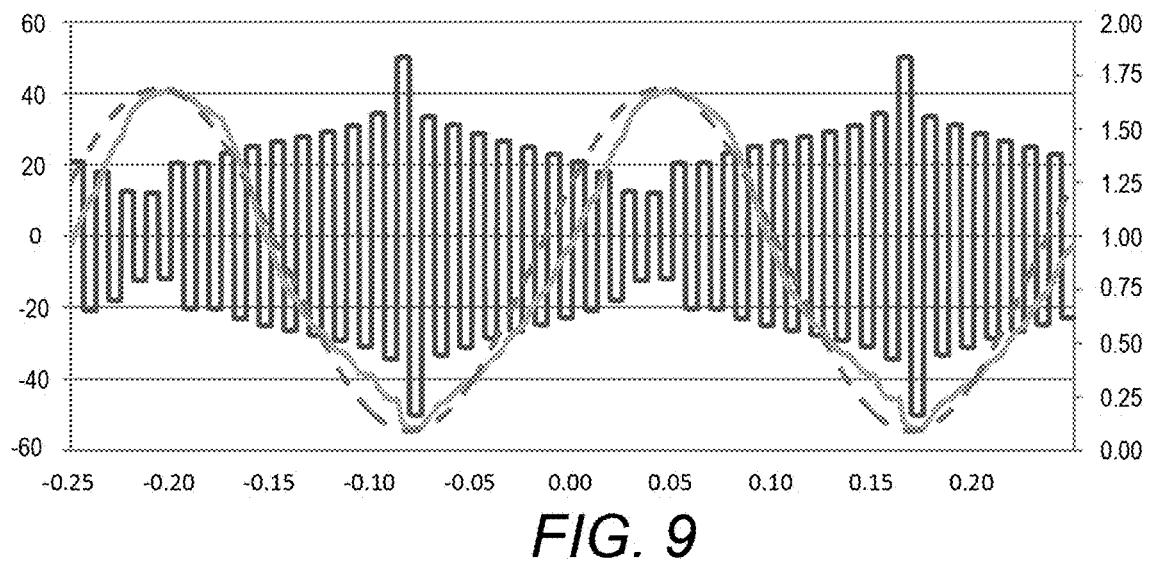
FIG. 9 is a graph illustrating an output of the polarized light in a case of applying a drive signal after correction to the polarization selection element of the present invention.

FIG. 9 is a graph illustrating the output of the polarized light in a case of applying a voltage corresponding to a rectangular wave before correction to the polarization selection element of the present invention. The left vertical axis of the graph of FIG. 9 indicates the voltage, the right vertical axis indicates the luminance, and the horizontal axis indicates the time.

As illustrated in FIG. 9, in the FFS liquid crystal panel, similarly to the TN liquid crystal panel, the change in luminance of measurement light that passes through the polarization selection element 120 does not coincide with the ideal sine wave.

Thus, the controller 140 performs the correction methods described in Embodiments 1 to 4 to eliminate the difference. The formulae and parameters to be used can be appropriately modified in accordance with the characteristics of the liquid crystal panel and the like.

In the FFS liquid crystal panel, the change in luminance of the polarized light when a voltage corresponding to the rectangular wave before correction is applied to the polarization selection element of the present invention substantially forms a sine wave, and therefore, the controller 140 may correct the offset of the phase instead.

According to Embodiment 5, effects similar to those of Embodiments 1 to 4 can be obtained even in the FFS liquid crystal panel.

The parameters included in the formulae described as examples in this specification may be appropriately modified depending on the liquid crystal viscosity, temperature, driving frequency and the like.

As set forth above, embodiments of this invention have been described; however, this invention is not limited to the foregoing embodiments. Although the embodiments have been described using a liquid crystal display device as a representative case, the display device can be a different display device such as an organic EL display device. Those skilled in the art can easily modify, add, or convert each element in the foregoing embodiment within the scope of this invention. A part of the configuration of one embodiment can be replaced with a configuration of another embodiment or a configuration of an embodiment can be incorporated into a configuration of another embodiment.

What is claimed is:

1. A polarization analysis apparatus, comprising:
   a light source that radiates first light causing a sample to be in an excitation state;
   a polarization selection element that outputs polarized light in a specific direction from second light radiated from the excited state sample in response to a voltage applied based on control information on a rectangular wave, the rectangular wave oscillates between positive and negative and an absolute value changes in a first cycle;
   an image sensor that measures a luminance of polarized light that has passed through the polarization selection element; and
   a controller that controls the polarization selection element and the image sensor,
   wherein the controller is configured to:
   calculate a reference voltage for each phase of the rectangular wave to cause the polarization selection element to output polarized light such that a change in luminance thereof forms a sine wave that oscillates in the first cycle;
   calculate a corrected reference voltage by correcting the reference voltage in at least one of two sections of the rectangular wave where an absolute value of the reference voltage increases in response to a phase change and where an absolute value of the reference voltage decreases in response to the phase change;
   generate the control information on the rectangular wave based on the reference voltage and the corrected reference voltage;
   apply a voltage to the polarization selection element based on the control information on the rectangular wave;
   operate the image sensor in accordance with a light exposure time having a time width obtained by dividing the first cycle by four, and measure luminance of polarized light output from the polarization selection element; and
   calculate a degree of polarization of the sample based on results of the measurement.

2. The polarization analysis apparatus according to claim 1, wherein the controller calculates the corrected reference voltage such that a correction amount gradually changes in accordance with the phase change of the rectangular wave.

3. The polarization analysis apparatus according to claim 2, wherein the controller is configured to:
   calculate the reference voltage based on Formula 1 where the reference voltage at phase p is V, a luminance of polarized light output from the polarization selection element at the phase p is H(p), a first adjustable parameter is k, and a second adjustable parameter is n; and
   calculate the corrected reference voltage by adding, to the reference voltage, a correction value calculated using a fractional function using the phase p as a variable:

Formula 1

$$V = k \times \left(\frac{H(p)}{1 - H(p)}\right)^{\frac{1}{n}} \qquad (1)$$

4. The polarization analysis apparatus according to claim 3, wherein the controller calculates the correction value using the fractional function given by Formula 2 where a third adjustable parameter is K, a fourth adjustable parameter is a, a fifth adjustable parameter is b, a sixth adjustable parameter is c, and a seventh adjustable parameter is d:

Formula 2

$$K \frac{(cp + d)}{p^2 + ap + b} \qquad (2)$$

5. The polarization analysis apparatus according to claim 2, wherein controller calculates the corrected reference voltage such that the correction amount gradually decreases from a start to an end of a section of a rectangular wave where an absolute value of a reference voltage increases in response to the phase change.

6. The polarization analysis apparatus according to claim 5, wherein the controller calculates the corrected reference voltage based on Formula 3 where the reference voltage at phase p is V, the corrected reference voltage at the phase p is V', and an eighth adjustable parameter is G, and
   wherein the eighth adjustable parameter satisfies Formula 4:

Formula 3

$$V' = V \times \exp((2-p) \times G) \qquad (3)$$

Formula 4

$$G \leq 0.3 \qquad (4)$$

7. The polarization analysis apparatus according to claim 5, wherein the controller calculates the corrected reference voltage based on Formula 5 where the reference voltage at phase p is V, the corrected reference voltage at the phase p is V', and a ninth adjustable parameter is q, and
   wherein the ninth adjustable parameter satisfies Formula 6:

Formula 5

$$V' = V \times (2-p)^q \qquad (5)$$

Formula 6

$$2 < q < 10 \qquad (6)$$

8. The polarization analysis apparatus according to claim 7, wherein the ninth adjustable parameter satisfies Formula 7:

Formula 7

$$q \approx 3.5 \qquad (7)$$

9. A control method for a polarization analysis apparatus that analyses polarized light radiated from a sample,
   the polarization analysis apparatus including: a light source that radiates first light causing a sample to be in an excitation state; a polarization selection element that outputs polarized light in a specific direction from second light radiated from the excited state sample in response to a voltage applied based on control information on a rectangular wave, the rectangular wave oscillates between positive and negative and an absolute value changes in a first cycle; an image sensor that measures a luminance of polarized light that has passed through the polarization selection element; and a controller that controls the polarization selection element and the image sensor, the control method for the polarization analysis apparatus comprising:

a first step in which the controller calculates a reference voltage for each phase of the rectangular wave to cause the polarization selection element to output polarized light such that a change in luminance thereof forms a sine wave that oscillates in the first cycle;

a second step in which the controller calculates a corrected reference voltage by correcting the reference voltage in at least one of two sections of the rectangular wave where an absolute value of the reference voltage increases in response to a phase change and where an absolute value of the reference voltage decreases in response to the phase change;

a third step in which the controller generates the control information on the rectangular wave based on the reference voltage and the corrected reference voltage;

a fourth step in which the controller applies a voltage to the polarization selection element based on the control information on the rectangular wave;

a fifth step in which the controller operates the image sensor in accordance with a light exposure time having a time width obtained by dividing the first cycle by four, and measures luminance of polarized light output from the polarization selection element; and a sixth step in which the controller calculates a degree of polarization of the sample based on results of the measurement.

10. The control method for a polarization analysis apparatus according to claim 9, wherein, in the second step, the controller calculates the corrected reference voltage such that a correction amount gradually changes in accordance with the phase change of the rectangular wave.

11. The control method for a polarization analysis apparatus according to claim 10, wherein, in the first step, the controller calculates the reference voltage based on Formula 8 where the reference voltage at phase p is V, a luminance of polarized light output from the polarization selection element at the phase p is H(p), a first adjustable parameter is k, and a second adjustable parameter is n; and wherein, in the second step, the controller calculates the corrected reference voltage by adding, to the reference voltage, a correction value calculated using a fractional function using the phase p as a variable:

Formula 8

$$V = k \times \left(\frac{H(p)}{1 - H(p)}\right)^{\frac{1}{n}} \quad (8)$$

12. The control method for a polarization analysis apparatus according to claim 11, wherein, in the second step, the controller calculates the correction value using the fractional function given by Formula 9 where a third adjustable parameter is K, a fourth adjustable parameter is a, a fifth adjustable parameter is b, a sixth adjustable parameter is c, and a seventh adjustable parameter is d:

Formula 9

$$K \frac{(cp + d)}{p^2 + ap + b} \quad (9)$$

13. The control method for a polarization analysis apparatus according to claim 10, wherein, in the second step, the controller calculates the corrected reference voltage such that the correction amount gradually decreases from a start to an end of a section of the rectangular wave where an absolute value of the reference voltage increases in response to the phase change.

14. The control method for a polarization analysis apparatus according to claim 13, wherein, in the second step, the controller calculates the corrected reference voltage based on Formula 10 where the reference voltage at phase p is V, the corrected reference voltage at the phase p is V', and an eighth adjustable parameter is G, and wherein the eighth adjustable parameter satisfies Formula 11:

Formula 10

$$V' = V \times \exp((2-p) \times G) \quad (10)$$

Formula 11

$$G \leq 0.3 \quad (11)$$

15. The control method for a polarization analysis apparatus according to claim 13, wherein, in the second step, the controller calculates the corrected reference voltage based on Formula 12 where the reference voltage at phase p is V, the corrected reference voltage at the phase p is V', and a ninth adjustable parameter is q, and wherein the ninth adjustable parameter satisfies Formula 13:

Formula 12

$$V' = V \times (2-p)^q \quad (12)$$

Formula 13

$$2 < q < 10 \quad (13)$$

16. The control method for a polarization analysis apparatus according to claim 15, wherein the ninth adjustable parameter satisfies Formula 14:

Formula 14

$$q \approx 3.5 \quad (14)$$

* * * * *